US00PP34058P2

(12) United States Plant Patent
Capo

(10) Patent No.: US PP34,058 P2
(45) Date of Patent: Mar. 22, 2022

(54) ***PETUNIA* PLANT NAMED 'KLEPH20425'**

(50) Latin Name: *Petunia hybrida*
Varietal Denomination: KLEPH20425

(71) Applicant: Klemm+Sohn GmbH & Co. KG, Stuttgart (DE)

(72) Inventor: Antonella Capo, Latina (IT)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/376,466

(22) Filed: Jul. 15, 2021

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Petunia* plant particularly distinguished by yellow petals with cherry color at margin of corolla, is disclosed.

1 Drawing Sheet

Genus and species: *Petunia hybrida.*
Variety denomination: 'KLEPH20425'.

BACKGROUND OF THE NEW PLANT

The present invention comprises a new and distinct variety of *Petunia*, botanically known as *Petunia hybrida* and hereinafter referred to by the variety name 'KLEPH20425'. 'KLEPH20425' is a selection from a cross-pollination of the proprietary female *Petunia* line 'PHT-2014-0059' (unpatented) and the commercial male *Petunia* line Surfina Star Rose (patent status not known).

In July of 2015, the proprietary female *Petunia* line 'PHT-2014-0059' and the male *Petunia* line Surfina Star Rose were cross pollinated in Latina, Italy and seeds were obtained. The seeds were sown and plants were grown for evaluation. A plant line was selected in April 2016 in Latina, Italy and named 'KLEPH20425'. In May 2016, 'KLEPH20425' was first vegetatively propagated by terminal tip cuttings and tissue culture in Latina, Italy. 'KLEPH20425' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Yellow petals with cherry color at margin of corolla.

DESCRIPTION OF THE PHOTOGRAPH

This new *Petunia* plant is illustrated by the accompanying photograph, which shows a close-up of the flower of the plant. The plant is about 12 weeks old grown in Stuttgart, Germany in January 2021. The colors shown are as true as can be reasonably obtained by conventional photographic procedures.

DESCRIPTION OF THE NEW VARIETY

The following detailed descriptions set forth the distinctive characteristics of 'KLEPH20425'. The data which define these characteristics were collected from asexual reproductions carried out in Latina, Italy. Data was collected on fourteen-week-old plants grown indoors in Latina, Italy under greenhouse conditions in May 2021. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH20425'.

Parentage:
- *Female.*—Proprietary *Petunia* line 'PHT-2014-0059'.
- *Male.*—Commercial *Petunia* line Surfina Star Rose.

Plant:
- *Form.*—Medium vigor.
- *Habit.*—Semi upright.
- *Height (from top of soil).*—18.0 cm.
- *Width (horizontal plant diameter).*—60.0 cm.
- *Propagation.*—Vegetative by terminal tip cuttings and tissue culture.
- *Time to produce a finished flowering plant.*—About14 weeks in winter under short day conditions, about 7 weeks in spring.
- *Time to initiate and develop roots.*—2 to 3 weeks.
- *Root description.*—Moderate density, moderate branching, white roots.

Stems:
- *Average number (basal).*—7.
- *Length of basal branches (from the base of the stem to the tip).*—40.0 cm.
- *Internode length.*—2.5 cm.
- *Diameter of branches (from midpoint).*—0.2 cm.
- *Stem color.*—RHS 144C.
- *Anthocyanin.*—Absent.
- *Texture.*—Pubescent.

Leaves:
- *Arrangement.*—Alternate along the stem and opposite under the inflorescence.
- *Length.*—3.5 cm.

*Width*.—2.0 cm.
*Shape*.—Ovate to elliptic.
*Apex*.—Obtuse.
*Base*.—Attenuate.
*Margin*.—Entire.
*Immature leaf color*.—Upper surface: RHS 137C. Lower surface: RHS 138B.
*Mature leaf color*.—Upper surface: RHS 137B. Lower surface: RHS 138B.
*Texture*.—Upper surface: Pubescent. Lower surface: Pubescent.
*Venation pattern*.—Arcuate.
*Venation color*.—Upper surface: RHS 137B. Lower surface: RHS 138B.
*Petioles*.—Length: 0.5 cm. Diameter: 0.3 cm. Color: RHS 144D. Texture: Pubescent.

Flower bud:
*Shape*.—Irregularly oblong.
*Length*.—4.3 cm.
*Diameter*.—0.6 cm.
*Color at tight bud*.—RHS 144C along the mid-veins, RHS N79A at the base and at the apex.
*Texture*.—Pubescent.

Inflorescence:
*Blooming habit (flowering season)*.—Continuously flowering during spring and summertime.
*Inflorescence type*.—Sympodial, with monochasial growth.
*Number of flowers per node*.—1.
*Lastingness of individual blooms on the plant*.—About 10 days.
*Fragrance*.—Absent.
*Flowers*.—Arrangement: Composed of 5 fused petals. Diameter (flower face): 5.5 cm. Depth (total length of flower): 5.5 cm. Throat/Funnel: Length: 3.0 cm. Diameter (at opening): 1.0 cm. Texture: Inner surface: Smooth. Outer surface: Pubescent. Color: Inner surface: RHS 153C. Outer surface: RHS N144D. Petals: Color, mature flower (fully opened): Upper surface: RHS N79C at corolla margin, RHS 149D along mid-veins. Lower surface: RHS N79D. Apex: Cuspidate. Base: Fused. Shape: Salverform. Margin: Entire. Strength of waviness: Weak. Degree of lobation: Medium.
*Calyx arrangement*.—Whorl of 5 sepals, fused at the base. Sepals: Color: Upper surface: RHS 137B. Lower surface: RHS 138A. Length: 1.5 cm. Width: 0.35 cm. Shape: Linear. Apex: Acute. Base: Attenuate. Margin: Entire. Texture: Upper surface: Pubescent. Lower surface: Pubescent.
*Pedicels*.—Color: RHS 144B. Length: 3.5 cm. Diameter: 0.1 cm. Texture: Pubescent.

Reproductive organs:
*Stamens*.—Quantity: 5. Shape: Needle with oblong head. Filament: Length: 1.4 cm. Diameter: 0.01 cm. Color: RHS 145C. Anther: Shape: Oblong. Color: RHS 195B. Length: 0.2 cm. Diameter: 0.15 cm. Pollen: Color: RHS 196C. Amount: Moderate.
*Pistils*.—Quantity per flower: 1. Length: 2.7 cm. Stigma color: RHS 139A. Style color: RHS 139D.

Fruit and seed set: None observed.
Disease and pest/insect resistance: None observed.

COMPARISON WITH PARENTAL LINES AND KNOWN VARIETY

'KLEPH20425' is a distinct variety of *Petunia*. 'KLEPH20425' is distinguished from its parents as described in Table 1:

TABLE 1

Comparison with Parental Lines

| Characteristic | Variety 'KLEPH20425' | Female parent 'PHT-2014-0059' | Male Parent Surfina Star Rose |
|---|---|---|---|
| Flower color and pattern | Yellow petals with cherry color at margin of corolla | Yellow petals with irregular red stripes along the fused parts of the corolla lobes | Rose petals with yellow star along mid-veins of |

'KLEPH20425' is most similar to the commercial *Petunia* plant named 'KLEPH16321' (not patented). Differences between the two varieties are described in Table 2:

TABLE 2

Comparison with Similar Variety

| Characteristic | Variety 'KLEPH20425' | Commercial line 'KLEPH16321' |
|---|---|---|
| Flower color and pattern | Yellow petals with cherry color at margin of corolla | Yellow petals with irregular cherry stripes along the fused parts of the corolla lobes |

I claim:

1. A new and distinct variety of *Petunia* plant named 'KLEPH20425' as illustrated and described herein.

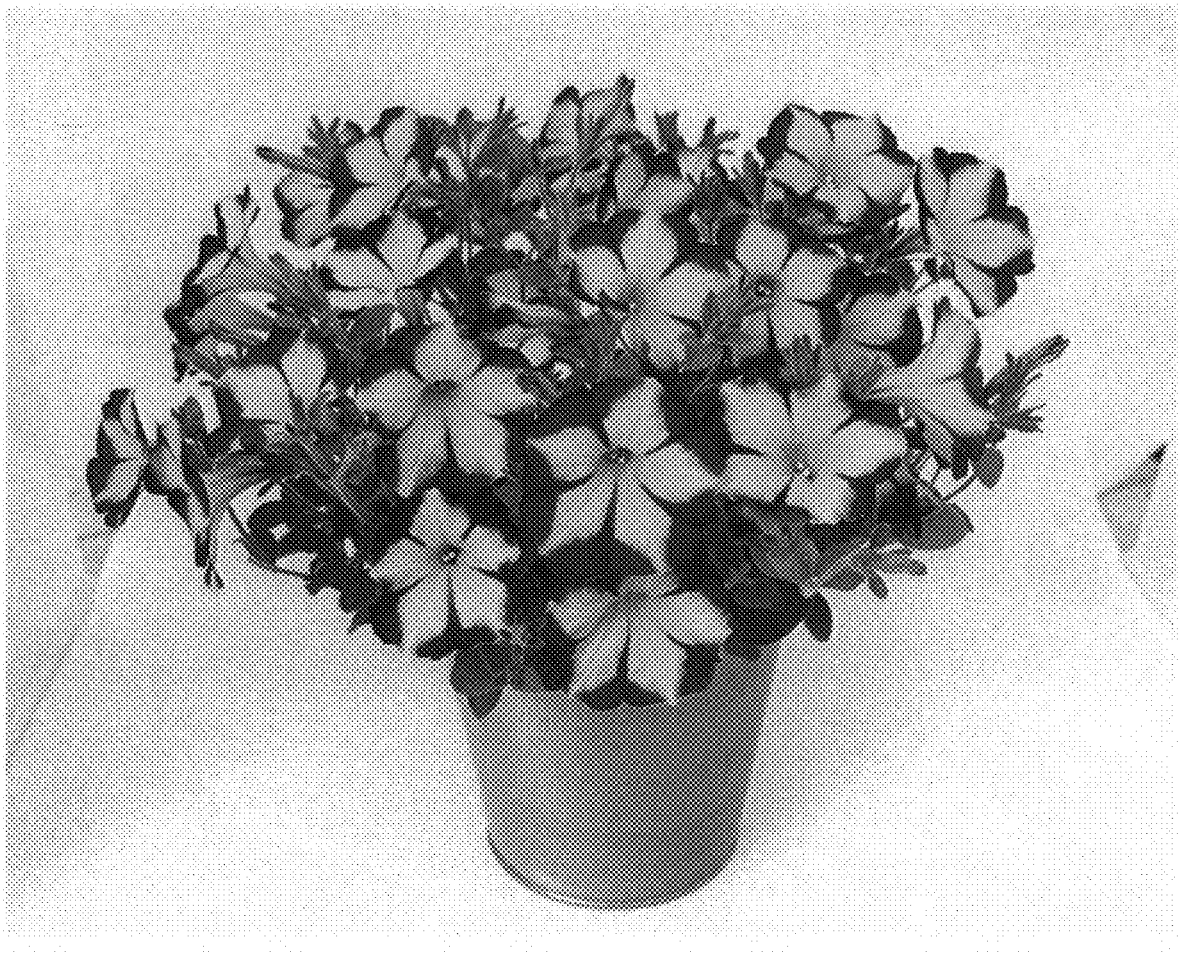

* * * * *